United States Patent [19]
Wilcox

[11] Patent Number: 4,696,668
[45] Date of Patent: Sep. 29, 1987

[54] DOUBLE BALLOON NASOBILIARY OCCLUSION CATHETER FOR TREATING GALLSTONES AND METHOD OF USING THE SAME

[76] Inventor: Gilbert M. Wilcox, 12 Towne Rd., Boxford, Mass. 01921

[21] Appl. No.: 756,065

[22] Filed: Jul. 17, 1985

[51] Int. Cl.$^4$ ............................................. A61M 25/00
[52] U.S. Cl. ....................... 604/28; 604/101; 128/24 A
[58] Field of Search ............... 604/101, 96, 102, 28, 604/49, 54; 128/344, 325, 345, 348.1, 673, 24 A

[56] References Cited

U.S. PATENT DOCUMENTS

| | | | |
|---|---|---|---|
| 4,030,505 | 6/1977 | Tessler | 128/24 A X |
| 4,224,929 | 9/1980 | Furihita | 128/6 X |
| 4,423,725 | 1/1984 | Baran et al. | 604/101 X |
| 4,445,892 | 5/1984 | Hussein et al. | 604/101 |
| 4,456,011 | 6/1984 | Warnecke | 604/101 X |
| 4,474,180 | 10/1984 | Angulo | 128/24 A X |
| 4,573,966 | 3/1986 | Weikl et al. | 604/101 X |

FOREIGN PATENT DOCUMENTS 683756 9/1979 U.S.S.R. .............. 604/101

*Primary Examiner*—Stephen C. Pellegrino
*Attorney, Agent, or Firm*—Michael J. Bevilacqua

[57] ABSTRACT

Disclosed is a double balloon multiple lumen nasobiliary occlusion catheter including two inflatable balloons positioned about the distal end of the catheter. The catheter comprises several lumens which are used for inflating and deflating the balloons, venting bile, and infusing and aspirating a dissolution solution. When inflated, the balloons occlude the lumen of the bile duct at two points thereby creating a sealed space between the balloons into which a treatment solution may be infused. Since this space is sealed from the remaining biliary tree, the treatment solution will find access to the gallbladder and any stones therein via the cystic duct with the exclusion of bile from the gallbladder fundus, or it will be confined in high concentration around bile duct gallstones located between the inflated balloons. While the treatment solution is applied to the gallstones, bile is excluded from the treatment site.

4 Claims, 4 Drawing Figures

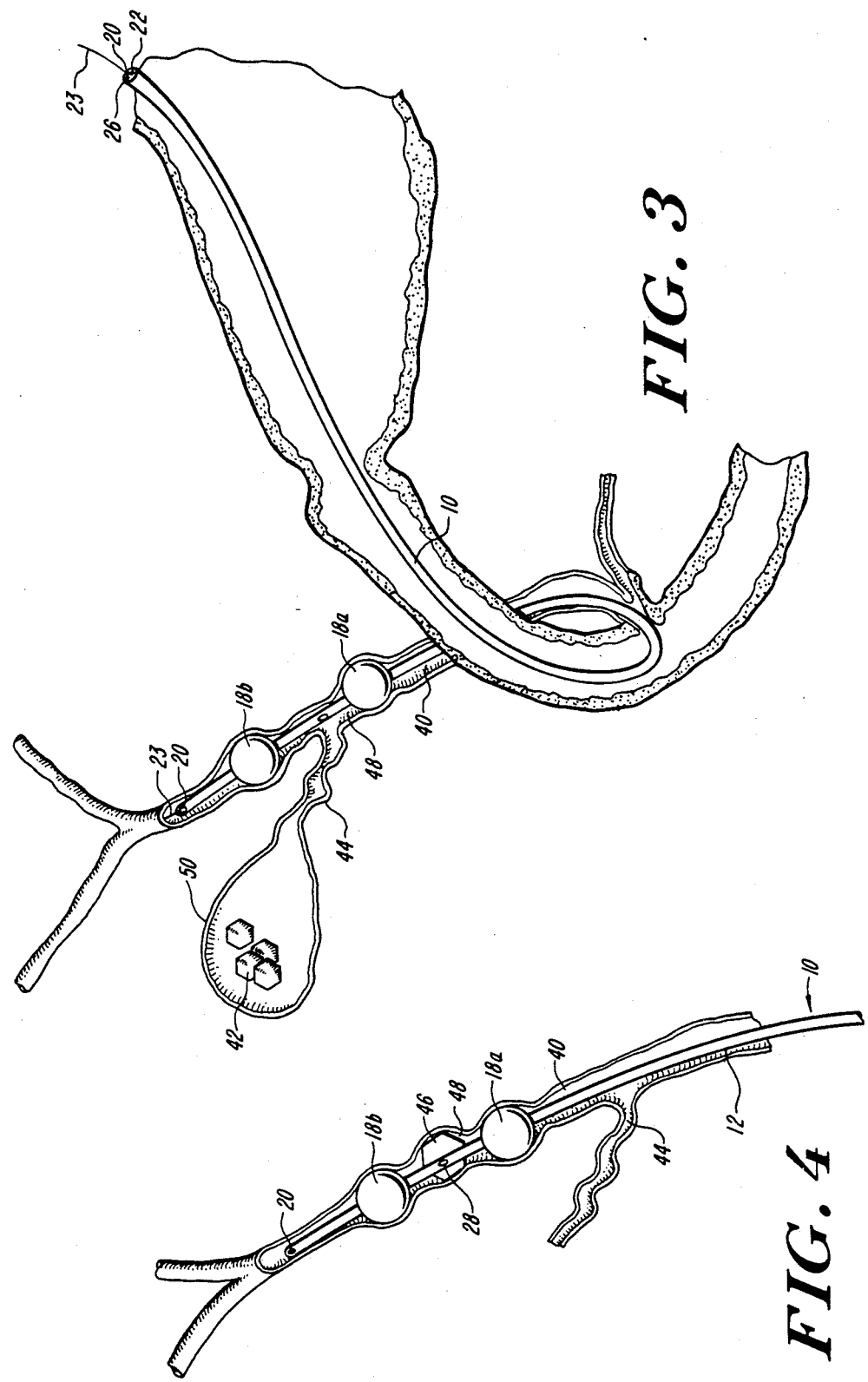

DOUBLE BALLOON NASOBILIARY OCCLUSION CATHETER FOR TREATING GALLSTONES AND METHOD OF USING THE SAME

BACKGROUND OF THE INVENTION

This invention relates to the treatment of gallstones and more particularly to a double balloon catheter and method of using a double balloon catheter for the treatment of gallstones.

In the past, gallstones have been treated with surgery, but this treatment is usually reserved for patients with gallstones producing symptoms. The operative techniques vary and may include cholecystectomy alone, or cholecystectomy combined with common duct exploration. Operative mortality rates vary with age and other comorbid conditions, and when elevated, make surgery an unattractive treatment.

In the last decade, treatment of gallstones by dissolution with orally administered bile acids such as chenodeoxycholic acid (CDCA) or ursodeoxycholic acid (UDCA) has been sucessfully accomplished. These agents work by inducing cholesterol unsaturation of bile. While dissolution of stones with orally administered bile acids eliminates many of the risks associated with surgery, many other problems are presented. First of all, complete dissolution occurs in only 30 to 40% of the patients (low index of efficacy). In addition, high doses of CDCA are required (15 mg/kg body wt/day resulting in doses of 1000 mg or more daily), and in order to achieve the dissolution, the duration of treatment must be rather long, i.e. on the order of 1 to 2 years. Furthermore, toxic side effects of the medications are encountered such as bile acid diarrhea, increase in serum cholesterol possibly leading to elevated cardiac risk, biochemical changes indicating liver abnormalities and changes in liver histology.

The infusion of monooctanoin (a dissolution agent) directly into the biliary tree by catheter has also been used to dissolve gallstones. Although this is a more direct method for dissolving gallstones than treatment with orally administered bile acids, monooctanoin is not a very effective solvent and dissolution times are on the order of days. This technique has therefore been reserved for large common duct stones which involve more extenuating clinical situations which eliminate other treatment options. Although bile exclusion and stirring are known to increase the effectiveness of monooctanoin, no device capable of excluding bile is currently used or available for treating gallstones with monooctanoin. Therefore, the monooctanoin is simply infused into the bile duct in the vicinity of the target gallstone with the patient's bile present.

Recently, methyl tertiary butyl ether (MTBE) has been shown to dissolve cholesterol gallstones much faster than either bile acids or monooctanoin. MTBE can dissolve gallstones about 50 times faster than monooctanoin in vitro. Furthermore, MTBE has, in fact, been instilled directly into the gallbladder by a catheter to successfully dissolve gallstones in humans. To do so, the catheter is placed into the gallbladder via a percutaneous transhepatic approach after a computed tomography scan of the liver with contrast enhancement demonstrates that the gallbladder has a sufficient area of attachment to the liver. In actual tests, the gallstones were successfully dissolved after seven hours of therapy in two patients, and another patent had only partial dissolution after 12 hours of treatment. The only ill effects suffered by these patients were mild pain and transient elevated white blood cell count (21,500) in one subject.

In view of the apparent advantages of using MTBE (or even monooctanoin) to dissolve gallstones, a need has developed to provide a means to deliver the MTBE to the gallbladder to dissolve the gallstones while at the same time excluding bile from the treatment area in a safe and effective manner. While catheters capable of delivering a dissolving agent to the gallbladder are currently known and available on the market, none of the known catheters are acceptable for this purpose since there are no known devices capable of excluding bile from the site of action of the dissolving agent or capable of directing or confining the dissolving agent to any particular site (e.g. the gallbaldder fundus).

An ERCP cannula, a single lumen plain catheter, is one such known catheter. It is generally constructed of clear plastic so one can visualize air bubbles. The tip of the catheter has graduated markings to gauge depth of insertion, and the catheters are approximately 200 centimeters in length with an outer diameter related to the size of the endoscope through which they are passed. No balloons are attached to these catheters and Luer locks are located on the proximal end so that after insertion through an endoscope they must be used with the endoscope in place. These catheters are used for diagnostic study of the common bile duct and the pancreatic duct by infusion of radiopaque dye through the catheter lumen.

Nasobiliary drain catheters are 200 to 300 centimeter long catheters (about 100 centimeters longer than ERCP catheters). The outer diameter is related to the size of the endoscope through which the catheter is passed, and the inner diameter must be large enough to allow passage over a guide wire. Nasobiliary drain catheters may have a pigtail distal end so the catheter will remain in place after the endoscope is removed. Often, such a catheter will include multiple holes at the distal end to facilitate infusion and drainage. These catheters are used for drainage of bile and infusion of medication into the common bile duct. Also, cholangiograms with dye may be done through a nasobiliary drain catheter. Unlike ERCP cannulae, the proximal end of these catheters have no Luer locks to allow the removal of the endoscope through which they were passed. There are no balloons at the distal end of these catheters for bile duct occlusion.

Another type of known catheter is the single balloon biliary occlusion catheter which is the same as an ERCP catheter except that a balloon is positioned at the distal end. These catheters are used for extraction of common bile duct stones and for the infusion of radiopaque dye into the biliary tree when an incompetent sphincter at the ampulla of Vater prevents retention of the dye. Thus, single balloon biliary occlusion catheters are used for diagnositic purposes. They have proximal Luer locks, and therefore they can only be used with an endoscope left in place.

None of the catheters described can be used for injecting a dissolving agent selectively into the gallbladder or a localized region of the common bile duct while at the same time being capable of excluding bile from the treatment area. In view of promising results obtained from the use of MTBE to dissolve gallstones the need for such a catheter has increased.

It is therefore a principal object of the present invention to provide a catheter for use in delivering and applying a dissolving agent to gallstones while at the same time preventing the passage of bile into the treatment area.

Another object of the present invention is to provide a catheter which will prevent or decrease loss of any dissolving agent either up into the biliary tree or down into common bile duct and pancreas or gastrointestinal tract via the Amulla of Vater.

An additional object of the present invention is to provide a catheter which is effective in treating gallstones lodged in either the gallbladder or the common bile duct.

A further object of the invention is to provide a catheter for infusing an agent around gallstones in the biliary tree.

A still further object of the present invention is to provide a catheter for use in the treatment of gallstones which is simple in construction and therefore cheaply manufactured.

Yet another object of the present invention is to provide a catheter for use in the treatment of gallstones which may be easily used in a safe manner without surgery or percutaneous needle aspiration of the gallbladder and their attendant complications.

SUMMARY OF THE INVENTION

A double balloon multiple lumen nasobiliary occlusion cather according to the present invention includes two inflatable balloons positioned about the distal end of the catheter. The catheter comprises several lumens which are used for inflating and deflating the balloons, venting bile, aspirating bile from the treatment site, and infusing and aspirating the dissolution solution.

When inflated, the balloons occlude the lumen of the bile duct at two points thereby creating a sealed space between the balloons into which a treatment solution may be infused. Since this space is sealed from the remaining biliary tree, the treatment solution will find access to the gallbladder and stones via the cystic duct with the exclusion of bile from the gallbladder fundus, or it will be confined in high concentration around bile duct gallstones located between the inflated balloons. While the treatment solution is applied to the gallstones, bile is excluded from the treatment site.

These and other objects and features of the present invention will become apparent from the following description which should be read in light of the accompanying drawings in which corresponding reference numerals identify corresponding parts throughout the several views.

BRIEF DESCRIPTION OF THE DRAWINGS

FIG. 3 is a view of the double balloon multiple lumen catheter of FIG. 1 inserted into a human body to treat gallstones located in the gallbladder;

FIG. 4 is a view of the double balloon bile exclusion catheter of FIG. 1 inserted into a human body to treat gallstones lodged in the common bile duct.

DETAILED DESCRIPTION OF THE PREFERRED EMBODIMENT

Figure 1:
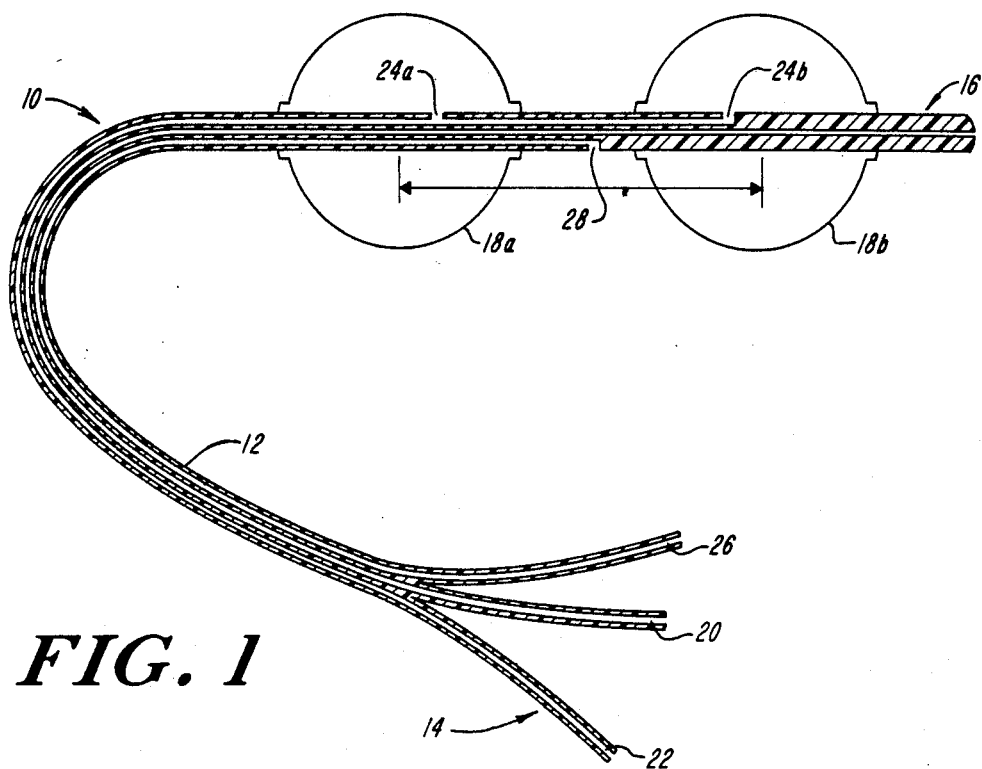
FIG. 1 is a sectional view of the double balloon multiple lumen bile exclusion catheter of the present invention.

The double balloon catheter 10 of the present invention shown in FIG. 1 includes a body portion 12 which extends from a proximal or external (outer) end 14 to a distal tip 16. Positioned at the distal end of the catheter are two balloons 18a, 18b which are inflatable to variable outer diameters. The two balloons may be of a type inflatable to a precisely controlled variable diameter, or the variable outer diameters may be obtained by using a series of catheters with balloons which are each inflatable to a series of fixed outer diameters.

The body 12 of the catheter according to the present invention includes several lumens. Lumen 20, which runs from the distal tip 16 to the proximal end 14, vents bile produced in the liver. Since lumen 20 runs the length of the catheter 10 it can accomodate a guide wire 23 (FIG. 3) to aid in the insertion and positioning of the catheter. Lumen 22 connects balloons 18a, 18b with the proximal end 14 of the catheter for inflation and deflation of the balloons. While shown in the embodiment of FIG. 1 as a single lumen, lumen 22 could be designed as a double lumen, one lumen of which is connected to each of the balloons 18a, 18b. Such a double lumen would allow independent inflation and deflation of the balloons. As shown in FIG. 1, lumen 22 is connected to the balloons through opening 24a in balloon 18a and opening 24b in balloon 18b. Infusion and aspiration lumen 26 is the third lumen shown in FIG. 1. Lumen 26 extends from the proximal end 14 of the catheter to an opening 28 which is located between the balloons 18a, 18b. In use, the dissolving solution is introduced through lumen 26; bile and cholesterol or other pigment laden dissolving solutions are aspirated through the lumen 26. As with lumen 22, lumen 26 may comprise two individual lumens—one for infusing the dissolving solution and one for aspirating bile, cholesterol, etc. When lumen 26 comprises two separate lumens, both lumens open between balloons 18a, 18b. The opening 28 may be comprised of multiple holes or perforations (not shown) located between the balloons and communicating with lumen 26. A grid or guard may be placed over the opening 28 to prevent aspiration of bile duct mucosa into the lumen 26.

The portion of the distal end 16 of the catheter 10 beyond balloon 18b, may have a pigtail configuration (not shown) to help stablize the catheter in the duct and prevent dislodgement of the catheter. The distal end 16 of the catheter may also have multiple perforations communicating with lumen 20. The proximal end 14 of the catheter will have no fixed Luer locks so that a duodenoscope may be removed over the catheter. Removable Luer locks may then be placed on the catheter ends.

Catheter 10 will generally have a length ranging from 200 cm to 400 cm. For transduodenoscopic catheters, the outer diameter corresponds to and is slightly smaller than the channel sizes of the available duodenoscopes. This is to allow passage through the duodenoscope channel. The extraduodenoscopic sizes are, however, not so restricted. The transduodenoscopic catheters may have an outside diameter ranging anywhere from 1.6 mm to 3.9 mm, and the extraduodenoscopic catheters may have an outside diameter ranging anywhere from 2.5 mm to 1.5 cm.

As discussed above, catheter 10 includes three lumens 20, 22, 26. A 2.4 mm outer diameter catheter will allow inner diameters of 0.7 mm, 0.7 mm and 1.0 mm respectively for lumens 20, 22 and 26. In alternate constructions, such as that where lumen 22 would actually consist of two lumens, each leading to one of openings 24a, and 24b, smaller lumen diameters would be necessitated.

Balloons 18a, 18b should be inflatable to a diameter of at least 2.5 cm for occlusion. Larger diameters may be necessary if there is dilation of the common bile duct. The placement of the distal balloon 18b from the distal tip 16 of the catheter 10 is not critical. A distance of 1 to 2 cm should be sufficient. The distance between balloons 18a and 18b along the catheter will be variable to allow for ease of placement of balloons above and below the cystic duct. The minimum distance between the balloon centers will be 2 cm and the usual distance will be about 3 cm, but the distance may be even greater. To facilitate placement about a high or low lying duct, alternate embodiments of the catheter may be employed with balloons inflatable to different sizes and placed differently along the catheter. The balloons may also be constructed to be of various shapes. Suitable balloons may be spherical, elliptical or elongated balloons with parallel sides. Balloons with irregular side contours may also be used.

The catheter body 12 and balloons 18a, 18b are constructed of materials which are insoluble in the dissolution solutions. In the preferred embodiments polyethylene and teflon are used. If MBTE is used for dissolution, then any components of the catheter which come into contact with dissolving solutions may not be made of latex or any other substance soluble in ether. The catheter body 12 and the balloons 18a, 18b will have radiopaque markers embedded in the construction materials allowing fluroscopic localization of the catheter and balloons.

Figure 2:
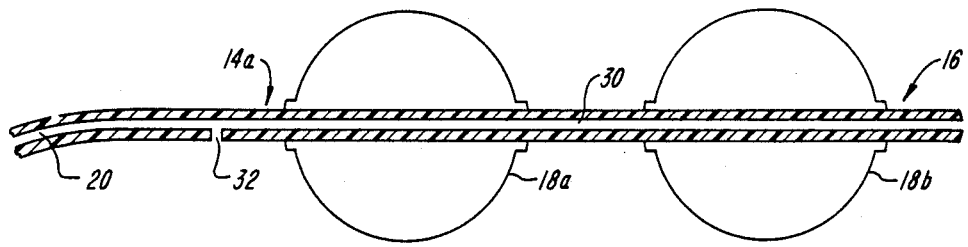
FIG. 2 is a sectional view of an alternate embodiment of the double balloon multiple lumen catheter shown in FIG. 1.

In an alternate embodiment of the catheter of the present invention shown in FIG. 2, a short segment bile (venting) bypass lumen 30 may be provided. In this catheter, the lumen used for the venting of bile has a short segment which courses from the distal tip 16 to the proximal side of balloon 18a where it reemerges out opening 32 in the side of the catheter. The original lumen 20, from distal tip to proximal-external end, should connect in line with this side venting lumen since such an arrangement will allow the passage of a guide wire down the catheter and out of the distal end. Such a side venting arrangement will cause less frictional drag to bile egress and allow the proximal portion of lumen 20 to be of a smaller diameter. (While not shown in FIG. 2, lumens 22, 26 would also be included in this emobodiment).

A still further embodiment of the catheter of the present invention includes a transducer which will generate ultrasonic vibrations. The transducer may be placed between the balloons, allowing ultrasonic energy to be incident upon the dissolving gallstones in the common bile duct or in the gallbladder causing more rapid dissolution by disturbing the unstirred layer of fluid around the gallstones and fragmentation of the stones. This may be especially useful in breaking up the original nidus of a stone as it becomes less than 50% of its original weight.

Another embodiment of the double balloon catheter 10 of the present invention incorporates a metal wire as part of the body 12 of the catheter. This wire would extend from the proximal end 14 to the distal tip 16. This wire may be embedded in the substance of the body 12 but not obstruct any of the lumens, or it may be bonded or attached to the exterior of the catheter body. This would give the catheter body more longitudinal and torsional strength which would prevent buckling of the catheter body under longitudinal force and would allow transmission of torsional force along the catheter more effectively.

The wire may be formed in a variable but obtuse angle, and the body 12 of the catheter would conform to such angulation. Alternatively, the body 10 of the catheter alone could be formed in a variable and obtuse angle. The obtuse angle would be created by the distal limb of the catheter with respect to the proximal catheter body. This would allow directional steering of the distal tip of the catheter by manipulating the proximal end with longitudinal or torsional forces (not shown).

The double balloon catheter 10 may also include the attachment of four wires which are intimately applied to or coursing through the body of the catheter but allowed to be freely movable. These wires are attached to the distal tip and thus one could deflect the distal tip by exerting a force on one wire directed toward the proximal end of the catheter while simultaneously decreasing the force on the opposing wire. One could then deflect the catheter tip in a desired direction and combined with longitudinal movement from applied force along the long axis of the catheter, accomplish direct navigation of the catheter in the bile duct.

Due to the non-uniform diameter of the common bile duct, variations in the level of entry of the cystic duct, or possible difficulties in positioning the balloons 18a, 18b around bile duct stones or the cystic duct entrance, it may be useful to allow the balloons to independently inflate to different diameters. Thus, if the cystic duct enters low (high) the proximal (distal) balloon 18a (18b) may be inflated to a smaller diameter independently in the smaller remaining length of the common bile duct, resulting in sealing of the intervening segment of the bile duct. Also, if the operator finds it difficult to precisely position the catheter with the balloons around a common bile duct stone, he may place the distal balloon 18b above the stone, inflate the balloon, and slowly withdraw the catheter until the stone is trapped. Then, inflation of the proximal balloon 18a will create the desired sealed space.

The balloon catheters described above may be used to treat gallstones in the gallbladder or bile ducts by dissolution. If the stones are in the gallbladder, then the cystic duct which allows entry of the dissolution solution must be patent. Such patency may be proven by oral cholecystogram or with radionucleotide scanning. The target stones must also be capable of dissolution with the intended therapeutic agent. For example, when using MTBE, the stones must be cholesterol stones, and they should not be pigment (bilirubin) stones.

The method of treating gallstones according to the present invention is implemented in the following manner with reference being made to FIGS. 3 and 4. First, a per oral endoscopic retrograde cholangiogram (ERC) is performed using a standard duodenoscope. This side viewing instrument may be a diagnostic or therapeutic type endoscope, and it will dictate the maximum size of the double balloon bile exclusion catheter allowable by the size of the endoscope channel (unless an extraduodenoscopic technique is used). The common bile duct 40 is cannulated and demonstrated by filling with dye. A guide wire 23 is inserted through the the ERC cannula into the common bile duct 40 and the ERC cannula is removed. Next, the double balloon bile exclusion catheter 10 is inserted into the common bile duct over the guide wire 23. The wire 23 will run through the bile venting lumen 20 from the proximal end 14 to the distal tip 16 where it will emerge. If gallbladder stones 42 are the target of dissolution, the balloons 18a, 18b are positioned one above and one below the cystic duct 44. If it is a common duct stone 46 which is to be dissolved, then the balloons 18a, 18b are positioned around the common duct stone 46 and a catheter of the type described above having independent inflatable balloons may be used.

Once the balloons 18a, 18b are in position, they are inflated thereby creating a sealed space 48 therebetween. The guide wire 23 is then removed, and dye may be infused into the space between the balloons to allow for checking the seal of the bile duct. If the seal is adequate, then the endoscope may be removed at this point, and the guide wire 23 may be reinserted to facilitate endoscope removal. Infusion-aspiration lumen 26 connected to the space between the balloons may now be aspirated, removing the bile from the gallbladder 50 or common duct 40 in continuity with target stones. The dissolving agent may then be infused into the sealed space 48 via the same infusion-aspiration lumen 26 through which the solution will find its way into the treatment area. If the stones are gallbladder stones, the solution will enter the gallbladder 50 via the cystic duct 44 to the target stones (because the sealed space 48 is in continuity with the cystic duct 44). Alternately, the solution may simply surround the target stones 46 in the common bile duct 40 when the stone is not a gallbladder stone. Bile will be excluded from the dissolusion site by the inflated balloons.

An alternate method of treating gallbladder or bile duct gallstones using the above described double balloon biliary occlusion catheter would use a percutaneous approach. First, a percutaneous transhepatic cholangiogram (PTC) is done using standard techniques. Next a guide wire is placed into the bile ducts through the PTC catheter and the PTC catheter is then removed leaving the guide wire in place in the bile ducts. Finally, the double balloon biliary occlusion catheter is introduced over the guide wire and positioned using fluroscopy and dye injection as described above. The catheter would function in a manner similar to that described for the peroral endoscopic method except that the catheter exits the body at the percutaneous site of entrance (not shown).

Dissolution of the stones may require multiple infusions and aspirations of the dissolving agent. If multiple infusions and aspirations are required and dissolution is not immediate, the catheter may be expected to be in place for 4 to 12 hours. This will require venting or removal of the expected 300-600 cc of hepatic bile produced in the proximal biliary tree during this time. The distal bile venting lumen 20 is intended to be used for this purpose. An alternate method of venting this bile (if the duration of treatment is long enough to require removal of bile) is to periodically deflate the balloons after removing the dissolving solution and let the bile escape spontaneously down the common bile duct and/or be aspirated up lumen 26. Such a situation does not, however, obviate the need for lumen 20 since the catheter will usually be placed over a guide wire through lumen 20. In an alternate embodiment of the present biliary occlusion catheter, lumen 20 may be omitted from the catheter, and such an omission would reccessitate (a) the ERC demonstrating the common bile duct be done with a standard ERCP cannula, next (b) the bile exclusion catheter be placed into the common bile duct without the assistance of a guide wire (which increases the difficulty of the procedure but does not render the procedure impossible) and (c) any bile requiring decompression in the proximal biliary tree be vented by balloon deflation.

A double balloon nasobiliary occlusion catheter for bile exclusion and gallstone dissolution has been described which will allow infusion and aspiration of therapeutic solutions into and out of the gallbladder while excluding these solutions from the rest of the biliary tree and gastrointestinal tract. As a result, the treated patient will be subject to a reduced exposure to the dissolving solutions and possibly less toxicity from these solutions. Furthermore, the treatment may be accomplished using endoscopic techniques thus avoiding surgery or percutaneous puncture methods for instilling dissolution solvents into the gallbladder. The patient therefore avoids the mortality and morbidity associated with surgical or percutaneous techniques.

The catheter of the present invention will very effectively treat gallstones since the sealing action of the balloons creates a space from which bile is excluded and in which a high concentration of the dissolving solution will be present. With bile excluded from the dissolution site, the efficiency of the dissolving solution of MTBE or monooctanoin (or any other agent in which a gallstone would be highly soluble while being relatively insoluable in bile) will be increased since the presence of bile is known to decrease the dissolution effect of these agents.

Finally, when the site of dissolution is small in volume (for example when the gallbladder is contracted or when dissolving stones in the common bile duct between the balloons), the volume of dead space in the infusion-aspiration lumen 26 may be large enough to allow a significant amount of bile to be reinfused into the dissolution site. As stated above, such bile will decrease the efficiency of dissolution. Also, any bile which might leak into the dissolution site would similarly hinder dissolution. The alternate embodiment in which there is an additional lumen so that there are separate lumens for infusion and aspiration will circumvent this problem since it will function with a zero dead space.

While the foregoing invention has been described with reference to its preferred embodiments, variations and modifications will occur to those skilled in the art. Such variations and modifications, as well as those described above, are intended to fall within the scope of the appended claims.

What is claimed is:

1. A method of dissolving gallstones lodged in the gallbladder of a human body with a dissolution agent, comprising the steps of:
   inserting a double balloon nasobiliary occlusion catheter into a human body in which gallstones have lodged in the gallbladder, said catheter having passages running therethrough for venting bile, for inflating and deflating balloons, and for infusing a dissolution agent and aspirating bile, cholesterol or other pigment laden dissolving solutions, said catheter being inserted so that the catheter extends into the common bile duct and common hepatic duct with a balloon positioned in the bile duct on each side of the entrance to the cystic duct;

inflating said balloons by forcing a fluid through said inflating and deflating passage, said balloons being inflated through a diameter greater than the diameter of the bile duct so as to isolate the portion of the bile duct between said balloons;

injecting a dissolution agent through said infusing and aspirating passage of said catheter into said isolated portion of the bile duct and into the cystic duct and gallbladder;

aspirating said dissolution agent and dissolved gallstones from said gallbladder and cystic duct through said infusing and aspirating passage of said catheter;

while said balloons are inflated, venting bile from the common hepatic duct through a distal end of said catheter through said bile venting passage of said catheter to the proximal end of said catheter;

once said gallstones are dissolved, deflating said balloons by allowing the inflating fluid to be discharged through said inflating and deflating passage, and withdrawing the catheter from the body.

2. The method of dissolving gallstones with a dissolution agent of claim 1 wherein said step of inserting a double balloon catheter comprises inserting a guide wire into the common bile duct and common hepatic duct of the body and passing the catheter over said guide wire through said body to its desired position in the common bile duct and common hepatic duct with the guide wire being positioned in the bile venting means.

3. The method of dissolving gallstones with a dissolution agent of claim 1 wherein said dissolution agent is methyl tertiary butyl ether.

4. The method of dissolving gallstones with a dissolution agent of claim 1 wherein said dissolution agent is monooctanoin.

* * * * *